United States Patent [19]

Lau et al.

[11] Patent Number: 4,859,667

[45] Date of Patent: Aug. 22, 1989

[54] PHARMACEUTICAL COMPOSITIONS OF PHENOTHIAZONE DERIVATIVES AND ANALOGS

[75] Inventors: Cheuk K. Lau, Pierrefonds; Christiane Yoakim, Montreal; Joshua Rokach, Laval; Rejean Fortin, Montreal; Yvan Guindon, Bizard, all of Canada

[73] Assignee: Merck Frosst Canada, Inc., Kirkland, Canada

[21] Appl. No.: 3,354

[22] Filed: Jan. 14, 1987

Related U.S. Application Data

[60] Division of Ser. No. 786,257, Oct. 10, 1985, Pat. No. 4,667,032, and a continuation-in-part of Ser. No. 559,471, Dec. 12, 1983, abandoned, which is a continuation-in-part of Ser. No. 536,487, Sep. 28, 1983, abandoned, which is a continuation-in-part of Ser. No. 459,924, Jan. 22, 1983, abandoned.

[51] Int. Cl.$^4$ .................... A61K 31/535; A61K 31/54
[52] U.S. Cl. .................... 514/224.5; 514/183; 514/212; 514/224.8; 514/229.5; 514/229.8; 514/250; 540/1; 540/481; 540/599; 544/14; 544/35; 544/37; 544/99; 544/102; 544/103; 544/104; 544/343; 544/347; 544/348
[58] Field of Search ............... 513/223, 212, 224, 183, 513/224.5, 229.5, 224.8, 229.8; 544/35, 37; 540/481, 599

[56] References Cited

U.S. PATENT DOCUMENTS

| | | | |
|---|---|---|---|
| 3,536,809 | 10/1970 | Applexweig | 424/28 |
| 3,598,123 | 8/1971 | Zaffaroni | 128/268 |
| 3,630,200 | 12/1971 | Higuchi | 128/260 |
| 3,845,770 | 11/1974 | Theeuwes et al. | 128/260 |
| 3,916,899 | 11/1975 | Theeuwer et al. | 128/260 |
| 4,008,719 | 2/1977 | Theeuwer et al. | 128/260 |
| 4,343,398 | 9/1987 | Atkinson et al. | 424/258 |

FOREIGN PATENT DOCUMENTS 0155623 9/1985 European Pat. Off. .
2247871 4/1973 Fed. Rep. of Germany .
48-22714 7/1973 Japan .

OTHER PUBLICATIONS

Chemical Abstracts, vol. 72, No. 13, 3-30-70 P.406 (Fujisawa) (1970).
Chemical Abstracts, vol. 90, No. 9, 2-26-79 P.133 (Ghizdavu) (1979).
Chemical Abstracts, vol. 78, No. 7, 2-19-73 P.485 (Shvedov) (1973).
Chemical Abstracts, vol. 92, No. 15, 4-14-80 P.12 (Mitchell) (1980).
Journal of the Chem. Soc. Perkin Transactionsi, No. 3 (1982).
Chemical Abstracts, vol. 99, No. 9 8-29-83 P.622 (Raileanu) (1983).
Terdic et al., Rev. Roum. Chim. 13 833 (1968).
Beckett et al., Xenobiotica 8 721 (1978).
Panea et al., Rev. Roum. Chim. 25 691 (1980).
Bhargave et al., Gazz. Chim. Ital. 110 201 (1980).
Bodea et al., Ann. Chem. 698 186 (1966).
Sugita et al., Nippon Kagaku Zasshi 89 309 (1968).
Broser et al., Rev. Roum. Chim. 17 1745 (1972).
Bodea et al., Ann. Chem. 715 122 (1968).
Bodea et al., Rev. Roum. Chim. 13 971 (1968).
Terdic et al., Rev. Roum. Chim. 13 1241 (1968).
Tsujino, Tet. Lett. (10) 763 (1969).
Roseboom et al., J. Pharm. Sci. 66 1395 (1977).
Fujisawa et al., Yakugaku Zasshi 86 541 (1966).
Bodea et al., Ann. Chem. 614 171 (1958).
McRae, Can. J. Med. Sci. 31 195 (1953).
Collier et al., Can. J. Med. Sci. 30 443 (1952).
Egan et al., Adv. Prost. Throm. Leuk. Res. 11 151 (1983).
Humes et al., J. Bio. Chem. 257 1591 (1982).
Winter et al., J. Pharm. Exp. Ther. 150 165 (1965).
Collier et al., Can. J. Biochem. 43 105 (1965).
Collier et al., Can. J. Biochem. 33 773 (1955).
Bailey et al., Ann. Rpts. Med. Chem. 16 213 (1981).
Baumann et al., Prostaglandins 20 627 (1980).
Collier et al., Can. J. Res. 20B 284 (1942).
Gordon et al., J. Counc. Sci. Ind. Res. (Aust.) 13 731 (1940).
Gallagher et al., Biochem. Pharm. 14 799 (1965).
Sircar et al., Biochem. Pharm., 32, No. 1, 170-172, 1983.
Hawkey et al., Prostaglandins Leukotrienes and Medicine, 10, 405-409, 1983.

*Primary Examiner*—Richard L. Raymond
*Attorney, Agent, or Firm*—Gabriel Lopez; Hesna J. Pfeiffer

[57] ABSTRACT

Phenothiazone derivatives and analogs thereof, pharmaceutical compositions and methods of treatment are disclosed. These compounds are useful as inhibitors of mammalian leukotriene biosynthesis. As such, these compounds are useful therapeutic agents for treating allergic conditions, asthma, cardiovascular disorders and inflammation.

25 Claims, No Drawings

PHARMACEUTICAL COMPOSITIONS OF PHENOTHIAZONE DERIVATIVES AND ANALOGS

CROSS REFERENCE TO RELATED APPLICATIONS

This is division of U.S. Ser. No. 786,257, filed Oct. 10, 1985, now U.S. Pat. No. 4,667,032 which is a continuation-in-part of application Ser. No. 559,471, filed Dec. 12, 1983, now abandoned, which is a continuation-in-part of application Ser. No. 536,487, filed Sept. 28, 1983, now abandoned, which is a continuation-in-part of application Ser. No. 459,924, filed Jan. 22, 1983, now abandoned.

U.S. Pat. No. 4,667,032 (Lau et al.) is incorporated herein by reference in its entirety.

DETAILED DESCRIPTION OF THE INVENTION

One embodiment of the present invention is a pharmaceutical composition containing a compound of the Formula I:

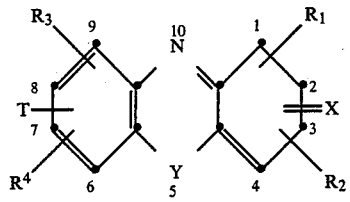

wherein

X is in the 1 or 3 position and is O, S or NR wherein R is H, $C_1$–$C_6$ branched or linear alkyl, CN or phenyl;

Y is O, Se, S, SO, $SO_2$ or NR; and the broken line represents an optical double bond between the 1 and 2 or 2 and 3 position;

$R_1$, $R_2$, $R_3$ and $R_4$ are independently selected from:
(1) hydrogen;
(2) alkyl having 1–6 carbon atoms;
(3) alkenyl having 2–6 carbon atoms;
(4) —$(CH_2)_n$M wherein n is 0–6 and M is
  (a) $OR_5$;
  (b) halogen;
  (c) $CF_3$;
  (d) $SR_5$ wherein $R_5$ is H; lower alkoxy-lower alkyl; lower acyloxy-lower alkyl; $C_1$–$C_6$ alkyl; benzyl; phenyl or substituted phenyl wherein the substituents are $C_1$–$C_3$ alkyl, halogen, CN, $CF_3$, $COOR_6$, $CH_2COOR_6$, $(CH_2)_nNR_8R_9$ wherein n is 0 to 2, $C_1$–$C_3$ alkoxy, OH, halo-$C_1$–$C_6$-alkyl; —$(CH_2)_mCOOR_6$, wherein m is 0 to 6 and $R_6$ is H, phenyl, or $C_1$–$C_6$ alkyl; CN; formyl; perfluoroalkyl; or $CH_2$-$R_{12}$ wherein n is 0 to 4, $R_{12}$ is $C_1$–$C_5$ alkyl, dimethylamino or phenyl;
  (e) phenyl or substituted phenyl as defined above for $R_5$;
  (f) $COOR_6$;
  (g)

wherein $R_{14}$ is H, $(CH_2)_nCOOR_6$ wherein n is 0 to 4, $C_1$–$C_6$ alkyl, $CF_3$, phenyl, or substituted phenyl as defined above for $R_5$;
(h) tetrazole;
(i)

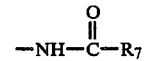

wherein $R_7$ is $C_1$–$C_6$ alkyl, benzyl or phenyl;
(j) —$NR_8R_9$ wherein $R_8$ and $R_9$ are independently selected from H, phenyl or substituted phenyl as defined above for $R_5$, $C_1$–$C_4$ alkyl, $C_1$–$C_4$ alkylamino alkyl, or may be joined through the N to form a heterocycloalkyl or 5–8 ring atoms;
(k) —$NHSO_2R_{10}$ wherein $R_{10}$ is OH, $C_1$–$C_6$ alkyl, $C_1$–$C_6$-alkoxy, phenyl, or $CF_3$;
(l)

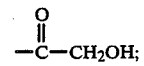

(m) —$SOR_{11}$ wherein $R_{11}$ is $C_1$–$C_6$ alkyl, phenyl or substituted phenyl as defined above for $R_5$, $(CH_2)_mCOOR_6$ wherein m is 1 to 6, CN, formyl or perfluoro-$C_1$–$C_4$ alkyl;
(n) —$CONR_8R_9$;
(o) —$SO_2NR_8R_9$;
(p) —$SO_2R_{13}$ wherein $R_{13}$ is OH, $C_1$–$C_6$ alkyl, H, phenyl or substituted phenyl as defined above for $R_5$, $(CH_2)_mCOOR_6$ wherein m is 1 to 6, CN, formyl or perfluoro-$C_1$–$C_4$ alkyl;
(q) $NO_2$;
(r)

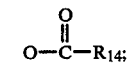

(s)

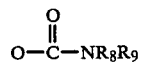

(t)

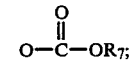

(u) CN;
(v) $NR_{15}R_{16}$ wherein $R_{15}$ and $R_{16}$ are such that $HNR_{15}R_{16}$ is an essential amino acid; or any two of $R_1$, $R_2$, $R_3$ and $R_4$ are joined (e.g. as —$(CH_2)_{3-4}$—) to add a fourth ring to the three ring structure, said ring having 5 or 6 carbon atoms and being saturated or unsaturated; and, T is H, halogen or $CF_3$.

The numbers surrounding Formula I designate the substituent positions. T, $R_1$, $R_2$, $R_3$ and $R_4$ may be positioned anywhere in the structure. As an example of compounds with a fourth ring, compounds of Formula II may be prepared by linking two of the substituent groups; $R_1$, $R_2$, $R_3$, $R_4$:

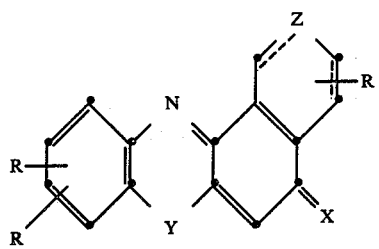

wherein Z may be CH, CH$_2$ or a bond, the broken lines represent optional double bonds and R represents the substituent groups of Formula I (R$_1$, R$_2$, R$_3$, R$_4$ and/or T) not used to create the fourth ring.

What is claimed is:

1. A pharmaceutical composition for inhibiting mammalian leukotriene biosynthesis or action containing a pharmaceutically acceptable carrier and an effective amount of a compound of the formula:

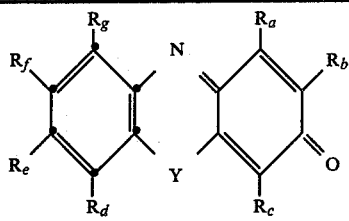

wherein the substituents are:

| Y | R$_a$ | R$_b$ | R$_c$ | R$_d$ | R$_e$ | R$_f$R$_g$ |
|---|---|---|---|---|---|---|
| S | H | SCH$_3$ | H | H | H | HH |
| S | H | H | SCF$_3$ | H | H | HH |
| S | H | H | CHO | H | H | HH |
| S | H | H | COCF$_3$ | H | H | HH |
| S | H | H | H | H | SCH$_3$ | HH |
| S | H | H | H | H | CO$_2$CH$_3$ | HH |
| S | H | H | H | H | CO$_2$H | HH |
| S | H | H | H | H | CHO | HH |
| S | H | H | H | H | CONH$_2$ | HH |
| S | H | H | H | H | CH$_2$OH | HH |
| S | H | H | Cl | H | Co$_2$Me | HH |
| S | H | H | Cl | H | CO$_2$H | HH |
| S | H | H | Cl | H | CHO | HH |
| S | H | H | Cl | H | COHN$_2$ | HH |
| S | H | H | Cl | H | CH$_2$OH | HH |
| S | H | O—benzyl | Cl | H | H | HH |
| S | H | OEt | Cl | H | F | HH |
| S | H | OEt | Cl | H | CH$_3$ | HH |
| S | CH$_3$ | H | Cl | H | CH$_3$ | HH |
| S | H | CH$_3$ | Cl | H | CH$_3$ | HH |
| S | H | OMe | Br | H | OMe | HH |
| S | H | OMe | Cl | H | OMe | HH |
| S | H | OEt | Br | H | OEt | HH |
| S | H | OEt | Cl | H | OEt | HH |
| S | H | OMe | Cl | H | OEt | HH |
| S | H | OMe | H | H | SMe | HH |
| O | H | OMe | Br | H | OMe | HH |
| O | H | OMe | Cl | H | OMe | HH |
| S | H | OMe | Br | H | Me | HH |
| SO$_2$ | H | H | OH | H | H | HH |
| SO$_2$ | H | OMe | OH | H | OMe | HH |
| SO$_2$ | OMe | OMe | Me | H | H | HH |
| SO$_2$ | H | H | OMe | H | H | HH |
| SO$_2$ | H | OMe | OMe | H | OMe | HH |
| S | OCH$_3$ | OCH$_3$ | Me | H | H | HH |
| S | H | H | COCH$_3$ | H | H | HH |
| S | OCH$_3$ | H | Br | H | OCH$_3$ | HH |
| S | OCH$_3$ | Cl | Cl | H | OCH$_3$ | HH |
| S | OCH$_3$ | H | Cl | H | OCH$_3$ | HH |
| S | H | ![piperazine-N-CH$_3$] | H | H | OCH$_3$ | HH |
| S | H | ![piperazine-N-CH$_3$] | Br | H | OCH$_3$ | HH |
| SO$_2$ | H | OCH$_3$ | OH | H | OCH$_3$ | HH |
| SO$_2$ | NHPr | H | NHPr | H | H | HH |
| SO$_2$ | H ![N-methylpiperazine] | H | ![N-methylpiperazine] | H | H | HH |
| SO$_2$ | H | OCH$_3$ | ![N-methylpiperazine] | H | OCH$_3$ | HH |
| SO$_2$ | H | OCH$_3$ | Br | H | OCH$_3$ | HH |
| S | NHPr | H | NHPr | H | H | HH |
| S | NHPr | H | NHPr | H | OCH$_3$ | HH |
| S | H | NHPr | NHPr | H | H | HH |
| S | H | NHPr | NHPr | H | OCH$_3$ | HH |
| S | H | OCH$_3$ | NH$_2$ | H | OCH$_3$ | HH |
| S | H | OCH$_3$ | NHPr | H | OCH$_3$ | HH |
| SO$_2$ | H | OCH$_3$ | NHPr | H | OCH$_3$ | HH |
| O | OCH$_3$ | H | Cl | H | OCH$_3$ | HH |
| O | OCH$_3$ | H | Br | H | OCH$_3$ | HH |
| O | NHPr | H | NHPr | H | H | HH |
| SO$_2$ | H | OCH$_3$ | CN | H | OCH$_3$ | HH |
| SO$_2$ | H | OCH$_3$ | NHCH$_2$CO$_2$R | H | OCH$_3$ | HH |
| SO$_2$ | H | OCH$_3$ | S—n-Bu | H | OCH$_3$ | HH |
| SO$_2$ | H | OCH$_3$ | CH$_2$CO$_2$R | H | OCH$_3$ | HH |
| SO$_2$ | H | OCH$_3$ | SO$_2$CH$_3$ | H | OCH$_3$ | HH |
| S | H | S—n-Bu | H | H | H | HH |
| S | H | H | S—n-Bu | H | H | HH |
| S | H | CH$_3$ | S—n-Bu | H | H | HH |
| S | H | OMe | Br | H | CF$_3$ | HH |
| S | H | OMe | Br | H | F | HH |
| S | H | OMe | Br | H | Cl | HH |
| S | H | OMe | Br | H | Br | HH |
| S | H | OMe | Br | H | NMe$_2$ | HH |
| S | H | OMe | Br | H | SMe | HH |
| S | H | OMe | Br | H | SO$_2$Me | HH |
| S | H | OMe | Br | H | Ph | HH | and R is H or C$_2$ to C$_4$alkyl.

2. A composition of claim 1 wherein the substituents are:

| Y | R$_a$ | R$_b$ | R$_c$ | R$_d$ | R$_e$ | R$_f$ | R$_g$ |
|---|---|---|---|---|---|---|---|
| S | H | OMe | Br | H | OMe | H | H |
| S | H | OMe | Cl | H | OMe | H | H |
| S | H | OEt | Br | H | OEt | H | H |
| S | H | OEt | Cl | H | OEt | H | H |
| S | H | OMe | Cl | H | OEt | H | H. |

3. A composition of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | OCH$_3$ | H | Br | H | OCH$_3$ | H | H |
| S | OCH$_3$ | Cl | Cl | H | OCH$_3$ | H | H |
| S | OCH$_3$ | H | Cl | H | OCH$_3$ | H | H. |

4. A composition of claim 1 wherein the substituents are:

| Y | $R_a$ | $R_b$ | $R_c$ | $R_d$ | $R_e$ | $R_f$ | $R_g$ |
|---|---|---|---|---|---|---|---|
| O | H | OMe | Br | H | OMe | H | H |
| O | H | OMe | Cl | H | OMe | H | H. |

5. A composition of claim 1 wherein the substituents are:

| Y | $R_a$ | $R_b$ | $R_c$ | $R_d$ | $R_e$ | $R_f$ | $R_g$ |
|---|---|---|---|---|---|---|---|
| O | OCH$_3$ | H | Cl | H | OCH$_3$ | H | H |
| O | OCH$_3$ | H | Br | H | OCH$_3$ | H | H. |

6. A composition of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | H | SCH$_3$ | H | H | H | H | H |
| S | H | H | H | H | SCH$_3$ | H | H |
| S | H | OMe | H | H | SMe | H | H |
| S | H | S—n-Bu | H | H | H | H | H |
| S | H | H | S—n-Bu | H | H | H | H |
| S | H | CH$_3$ | S—n-Bu | H | H | H | H |
| S | H | OMe | Br | H | SMe | H | H |
| S | H | OMe | Br | H | SO$_2$Me | H | H. |

7. A composition of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | H | H | H | H | CO$_2$CH$_3$ | H | H |
| S | H | H | H | H | CO$_2$H | H | H |
| S | H | H | H | H | CONH$_2$ | H | H |
| S | H | H | Cl | H | CO$_2$Me | H | H |
| S | H | H | Cl | H | CO$_2$H | H | H |
| S | H | H | Cl | H | CONH$_2$ | H | H |
| SO$_2$ | H | OCH$_3$ | CH$_2$CO$_2$R | H | OCH$_3$ | H | H. |

8. A composition of claim 1 wherein the substituents are:

9. A composition of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | H | OCH$_3$ | NH$_2$ | H | OCH$_3$ | H | H |
| S | H | OCH$_3$ | NHPr | H | OCH$_3$ | H | H |
| SO$_2$ | H | OCH$_3$ | NHCH$_2$CO$_2$R | H | OCH$_3$ | H | H. |

10. A composition of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | H | H | H | H | CHO | H | H |
| S | H | H | H | H | CH$_2$OH | H | H |
| S | H | H | Cl | H | CHO | H | H |
| S | H | H | Cl | H | CH$_2$OH | H | H. |

11. A composition of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | NHPr | H | NHPr | H | H | H | H |
| S | NHPr | H | NHPr | H | OCH$_3$ | H | H |
| S | H | NHPr | NHPr | H | H | H | H |
| S | H | NHPr | NHPr | H | OCH$_3$ | H | H |
| O | NHPr | H | NHPr | H | H | H | H. |

12. A composition of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | H | OEt | Cl | H | CH$_3$ | H | H |
| S | H | OMe | Br | H | Me | H | H |

-continued

| Y | $R_a$ | $R_b$ | $R_c$ | $R_d$ | $R_e$ | $R_f$ | $R_g$ |
|---|---|---|---|---|---|---|---|
| S | H | OMe | Br | H | $CF_3$ | H | H |
| S | H | OMe | Br | H | F | H | H |
| S | H | OMe | Br | H | Cl | H | H |
| S | H | OMe | Br | H | Br | H | H |
| S | H | OMe | Br | H | $NMe_2$ | H | H |
| S | H | OMe | Br | H | Ph | H | H. |

13. A composition of claim 1 wherein the substituents are:

| Y | $R_a$ | $R_b$ | $R_c$ | $R_d$ | $R_e$ | $R_f$ | $R_g$ |
|---|---|---|---|---|---|---|---|
| $SO_2$ | H | H | OH | H | H | H | H |
| $SO_2$ | H | OMe | OH | H | OMe | H | H |
| $SO_2$ | OMe | OMe | Me | H | H | H | H |
| $SO_2$ | H | H | OMe | H | H | H | H |
| $SO_2$ | H | OMe | OMe | H | OMe | H | H |
| $SO_2$ | NHPr | H | NHPr | H | H | H | H |
| $SO_2$ | H | $OCH_3$ | Br | H | $OCH_3$ | H | H |
| $SO_2$ | H | $OCH_3$ | NHPr | H | $OCH_3$ | H | H |
| $SO_2$ | H | $OCH_3$ | CN | H | $OCH_3$ | H | H |
| $SO_2$ | H | $OCH_3$ | S—n-Bu | H | $OCH_3$ | H | H |
| $SO_2$ | H | $OCH_3$ | $SO_2CH_3$ | H | $OCH_3$ | H | H. |

14. A composition of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | H | H | CHO | H | H | H | H |
| S | H | H | $COCF_3$ | H | H | H | H |
| S | H | O—benzyl | Cl | H | H | H | H |
| S | $CH_3$ | H | Cl | H | $CH_3$ | H | H |
| S | H | $CH_3$ | Cl | H | $CH_3$ | H | H |
| S | $OCH_3$ | $OCH_3$ | Me | H | H | H | H |
| S | H | H | $COCH_3$ | H | H | H | H. |

15. A composition of claim 1 wherein the compound is: 4-bromo-2,7-dimethoxy-3H-phenothiazin-3-one.

16. A composition of claim 1 wherein the compound is: 4-chloro-2,7-dimethoxy-3H-phenothiazin-3-one.

17. A composition of claim 1 wherein the compound is: 4-bromo-2,7-diethoxy-3H-phenothiazin-3-one.

18. A composition of claim 1 wherein the compound is: 4-chloro-2,7-diethoxy-3H-phenothiazin-3-one.

19. A composition of claim 1 wherein the compound is: 4-bromo-2,7-dimethoxy-3H-phenoxazin-3-one.

20. A composition of claim 1 wherein the compound is: 4-chloro-2,7-dimethoxy-3H-phenoxazin-3-one.

21. A pharmaceutical composition for inhibiting mammalian luekotrine biosynthesis or action containing a pharmaceutically acceptable carrier and an effective amount of a compound of the formula:

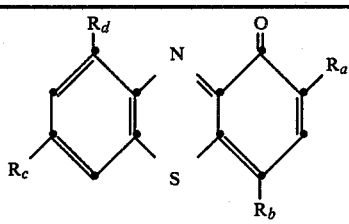

wherein the substituents are:

| $R_a$ | $R_b$ | $R_c$ | $R_d$ |
|---|---|---|---|
| t-Bu | t-Bu | H | H |
| t-Bu | t-Bu | F | H |
| t-Bu | t-Bu | Me | H |

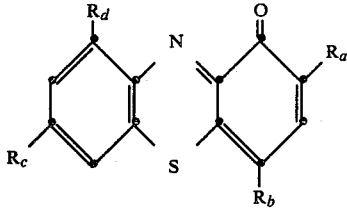

wherein the substituents are:

| $R_a$ | $R_b$ | $R_c$ | $R_d$ |
|---|---|---|---|
| t-Bu | t-Bu | SMe | H |
| t-Bu | t-Bu | H | OMe |

22. 2-S-glutathionyl-3H-phenothiazin-3-one; or 4-chloro-2-S-glutathionyl-phenothiazin-3-one.

23. A pharmaceutical composition for inhibiting mammalian luekotrine biosynthesis or action containing a pharmaceutically acceptable carrier and an effective amount of a compound of the formula:

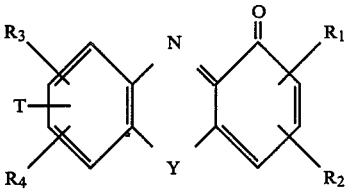

wherein the substituents are:

| Y | $R_1$ | $R_2$ |
|---|---|---|
| S, SO, or $SO_2$ | 2-Cl | H |
| " | 2-$SCF_3$ | H |
| " | 2-S-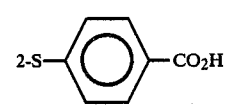-$CO_2H$ | H |
| S | 2-t-Bu | 4-t-Bu |
| S, SO, or $SO_2$ | 2-CN | H |
| " | H | 3-$CO_2Et$ |
| " | H | 3-Cl |
| " | H | H |
| " | H | H |
| " | 2-Cl | H |
| S | H | H |
| S | 2-Cl | 3-Cl |
| S | 2-Br | 3-Br |
| S | H | H |
| S | 2-Cl | H |
| S | 2-F | H |
| S | 2-Br | H |
| S | 2-$CF_3$ | H |
| S | 2-$SCF_3$ | H |
| S | 2-$SO_2CF_3$ | H |
| S | H | 3-Cl |
| S | H | 3-$CO_2Et$ |
| S | H | 3-$CO_2H$ |
| S | H | 3-CN |
| S | H | 3-$SCF_3$ |
| S | H | H |
| S | H | H |
| S | 2-Br | H |
| S | 2-Cl | H |
| S | 2-Cl | H |
| S | 2-Cl | H |
| S | 2-Cl | H |
| S | H | 3-$CONMe_2$ |
| S | 2-Cl | H |

-continued

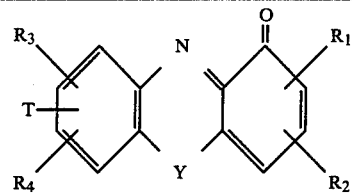

wherein the substituents are:

| Y | R1 | R2 |
|---|----|----|
| S | 2-S-C6H4-CO2H (para) | H |
| S | 2-SO2CH3 | H |
| S | 2-CH2CH=CH2 | H |
| S | H | 3-N(CH3)2 |
| S | 2-CH2CO2H | H |
| S | 2-Cl | H |
| S | 2-COCH3 | H |
| S | H | H |
| S | 2-COCH3 | H |
| S | H | H |
| S | 4-Cl | H |
| SO | H | H |
| SO2 | H | H |
| SO2 | 4-Cl | H |
| S | 2-t-Bu | 9-t-Bu |
| S | 2-t-Bu | 7-t-Bu |
| S | 2-t-Bu | 7-t-Bu |
| S | 2-t-Bu | 7-t-Bu |

| R3 | R4 | T |
|----|----|---|
| H | H | H |
| H | H | H |
| H | H | H |
| H | H | H |
| H | H | H |
| H | H | H |
| H | H | H |
| H | H | H |
| 4-Cl | H | H |
| 4-SO2CH3 | H | H |
| 4-Cl | H | H |
| H | H | H |
| 4-Cl | 7-Cl | 9-Cl |
| 4-Br | 7-Br | 9-Br |
| H | 7-SO2CH3 | H |
| 4-SO2CH3 | H | H |
| 4-Cl | H | H |
| H | H | H |
| H | H | H |

-continued

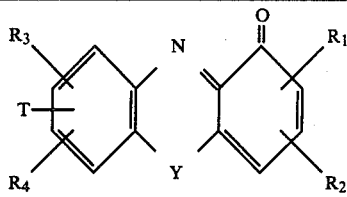

wherein the substituents are:

| R1 | R2 | R3 |
|----|----|----|
| H | H | H |
| H | H | H |
| H | H | H |
| H | H | H |
| H | H | H |
| 4-Cl | H | H |
| 4-SCF3 | H | H |
| 4-Br | H | H |
| H | 8-CN | H |
| H | 8-CO2Et | H |
| H | 8-CO2H | H |
| H | 8-CF3 | H |
| H | 7-SO2CH3 | H |
| H | H | H |
| H | 7-OCH3 | H |
| H | H | H |
| 4-CH2CH=CH2 | H | H |
| H | H | H |
| 4-Cl | 7-S—C6H5 | H |
| H | H | H |
| 4-SCH2CO2H | H | H |
| H | H | 7-CF3 |
| 4-CO—C6H5 | H | 7-CF3 |
| H | H | H |
| H | 7-OCH3 | H |
| 4-COC6H5 | 7-OCH3 | H |
| H | H | H |
| H | H | H |
| H | H | H |
| 4-OMe | H | H |
| 4-F | H | H |
| 4-Me | H | H |
| 4-SMe | H | H |

24. A pharmaceutical composition for inhibiting mammalian luekotrine biosynthesis or action containing a pharmaceutically acceptable carrier and an effective amount of a compound of the formula:

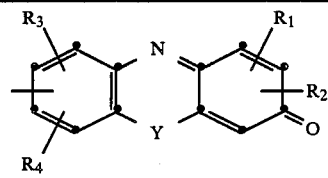

wherein the substituents are

| R1 | R2 | R3 | R4 | T |
|----|----|----|----|---|
| 2-N(Me)2 | H | H | H | H |
| 2-SMe | H | H | H | H |
| 2-S—pPAA | H | H | H | H |
| 2-C(O)CH3 | H | H | H | H |
| H | 2-SO3H | H | H | H |
| H | H | 7-OH | 6-propyl | H |
| 4-Cl | 1-CH2COOH | H | H | H |
| 4-Cl | 2-CH2COOH | H | H | H |
| 4-OH | 2-OMe | 7-OMe | H | H |
| 4-Me | 1-OMe | 2-OMe | H | H |
| 4-Cl | H | 6-CH2COOH | H | H |
| 4-Cl | H | 7-CH2COOH | H | H |
| 4-Cl | H | 8-CH2COOH | H | H |

-continued

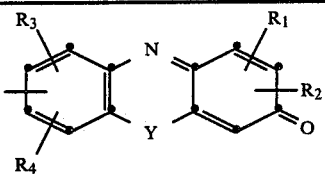

wherein the substituents are

| R₁ | R₂ | R₃ | R₄ | T |
|---|---|---|---|---|
| 4-Cl | 2-N(Me)₂ | H | H | H |
| 4-Cl | 1-N(Me)₂ | H | H | H |
| 4-Cl | 2-N(Me)₂ | 7-OMe | H | H |
| 4-Cl | 2-N(Me)₂ | 7-Cl | H | H |
| 4-Cl | 2-SMe | H | H | H |
| 4-Cl | 2-SCH₂COOH | H | H | H |
| 4-Cl | 2-S—pPAA | H | H | H |
| 4-Cl | 1-S—pPAA | H | H | H |
| 4-Cl | 2-S—pPAA | 7-OMe | H | H |
| 4-Cl | 2-SO₃H | H | H | H |
| 4-Cl | 2-OMe | 7-Cl | H | H |
| 4-OMe | 2-SMe | H | H | H |
| 4-SMe | H | H | H | H |
| 4-Cl | H | ⁷⁄₈-(CH₂)₄— | | H |
| 4-Cl | H | ⁷⁄₈-(CH₂)₃— | | H |
| 4-Br | 2-OMe | 7-OMe | H | H |
| 7-NH₂ | H | H | H | H |
| 2-Me | 7-N(Me)₂ | H | H | H |
| 7-N(Me)₂ | H | H | H | H |
| 1-CO₂H | 4-OH | 7-NMe₂ | H | H |
| 1-Me | 7-Me | H | H | 4-Cl |
| 2-Me | 7-Me | H | H | 4-Cl |
| 1-OMe | 2-OMe | 7-Me | H | H |
| 2-OMe | 7-SMe | H | H | H |
| 4-COMe | H | H | H | H |
| 2 n-Bu | H | H | H | H |
| 4-S—n-Bu | H | H | H | H |
| 2-Me | 4-S—n-Bu | H | H | H |
| 1-OMe | 2-OMe | 4-Me | H | H |
| 1-OMe | 7-OMe | H | H | 4-Br |
| 1-OMe | 7-OMe | 2-Cl | H | 4-Cl |
| 1-OMe | 7-OMe | H | H | 4-Cl |
|  | 7-OMe | H | H | H |
|  | 7-OMe | H | H | 4-Br |
| 2-OMe | 4-OH | 7-OMe | H | H |
| 1-NHPr | 4-NHPr | H | H | H |
|  |  | H | H | H |
| 4-COMe | H | H | H | H |
| 2-NHPr | 4-NHPr | H | H | H |
| 2-OME | 4-CN | 7-OMe | H | H |
| 2-OMe |  | 7-OMe | H | H |
| 2-OMe | 4-NHPr | 7-OMe | H | H |
| 1-NHPr | 4-NHPr | H | H | H |
| 1-NHPr | 4-NHPr | 7-OMe | H | H |
| 2-NHPr | 4-NHPr | 7-OMe | H | H |
| 2-OMe | 4-NH₂ | 7-OMe | H | H |
| 2-OMe | 4-NHPr | 7-OMe | H | H |

-continued

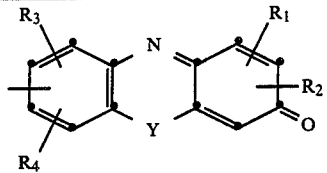

wherein the substituents are

| R₁ | R₂ | R₃ | R₄ | T |
|---|---|---|---|---|
| 1-OMe | 4-Cl | 7-OMe | H | H |
| 1-OMe | 4-Br | 7-OMe | H | H |
| 1-OMe | 4-CN | 7-OMe | H | H |
| 2-OMe | 4-NHCH₂CO₂R | 7-OMe | H | H |
| 2-OMe | 4-S—n-Bu | 7-OMe | H | H |
| 2-OMe | 4-CH₂CO₂R | 7-OMe | H | H |
| 2-OMe | 4-SO₂Me | 7-OMe | H | H |
| 2-S—n-Bu | H | H | H | H |
| 4-S—n-Bu | H | H | H | H |
| 2-Me | 4-S—n-Bu | H | H | H |
| 2-OMe | 7-Me | H | H | 4-Br |
| 2-OMe | 7-CF₃ | H | H | 4-Br |
| 2-OMe | 7-F | H | H | 4-Br |
| 2-OMe | 7-Cl | H | H | 4-Br |
| 2-OMe | 7-Br | H | H | 4-Br |
| 2-OMe | 7-NMe₂ | H | H | 4-Br |
| 2-OMe | 7-SMe | H | H | 4-Br |
| 2-OMe | 7-SO₂Me | H | H | 4-Br |
| 2-OMe | 7-Ph | H | H | 4-Br |
| 1-Me | 7-Me | H | H | 4-Cl |
| 2-NH₂ | H | H | H | H | where Y is S, SO, or SO₂;
pPAA is paraphenylacetic acid; and
R is H or C₁ to C₄ alkyl.

25. A pharmaceutical composition for inhibiting mammalian luekotrine biosynthesis or action containing a pharmaceutically acceptable carrier and an effective amount of a compound of the formula:

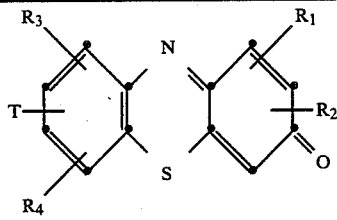

wherein the substituents are:

| R₁ | R₂ | R₃ | R₄ | T |
|---|---|---|---|---|
| 2-OMe | 7-OMe | H | H | 1-Br |

-continued

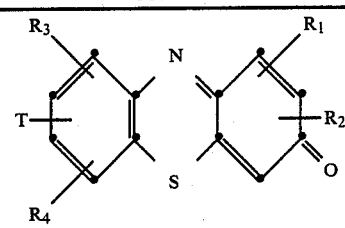

wherein the substituents are:

| R₁ | R₂ | R₃ | R₄ | T |
|---|---|---|---|---|
| 1-OMe | 7-OMe | H | H | 2-Br |
| 1-OMe | 7-OMe | H | H | 4-Br |
| 1-OMe | 7-OMe | H | H | 2-Cl |
| 1-OMe | 7-OMe | H | H | 4-Cl |
| 2-OMe | 7-OMe | H | H | 1-Cl |
| 2-OMe | 7-OMe | H | H | 4-Cl |
| 2-OEt | 7-OEt | H | H | 1-Br |
| 2-OEt | 7-OEt | H | H | 4-Br |
| 2-OEt | 7-OEt | H | H | 1-Cl |
| 2-OEt | 7-OEt | H | H | 4-Cl |
| 2-OMe | 7-OMe | 8-OMe | H | 1-Br |
| 2-OMe | 7-OMe | 8-OMe | H | 4-Br |
| 2-OMe | 7-OMe | H | H | 4-F |
| 2-OMe | 7-OMe | H | H | 4-CF₃ |
| 2-OMe | 7-OEt | H | H | 4-Br |
| 2-OMe | 7-OEt | H | H | 4-Cl |
| 2-OMe | 7-OEt | H | H | 4-F |
| 2-OMe | 7-OEt | H | H | 4-CF₃ |
| 2-OEt | 7-OMe | H | H | 4-Br |
| 2-OEt | 7-OMe | H | H | 4-Cl |
| 2-OEt | 7-OMe | H | H | 4-F |
| 2-OEt | 7-OMe | H | H | 4-CF₃ |
| 2-OMe | 7-OMe | H | H | 4-Br |

* * * * *